United States Patent
Yan et al.

(10) Patent No.: US 11,723,632 B2
(45) Date of Patent: Aug. 15, 2023

(54) WORKFLOW OF NEEDLE TIP IDENTIFICATION FOR BIOPSY DOCUMENTATION

(71) Applicant: KONINKLIJKE PHILIPS N.V., Eindhoven (NL)

(72) Inventors: Pingkun Yan, Gaithersburg, MD (US); Jochen Kruecker, Andover, MA (US); Scott Frederic Thompson, Gainesville, FL (US); Wei Lin, Gainesville, FL (US); Samuel Coons, Gainesville, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1193 days.

(21) Appl. No.: 15/747,161

(22) PCT Filed: Jul. 18, 2016

(86) PCT No.: PCT/IB2016/054259
§ 371 (c)(1),
(2) Date: Jan. 24, 2018

(87) PCT Pub. No.: WO2017/017556
PCT Pub. Date: Feb. 2, 2017

(65) Prior Publication Data
US 2018/0214139 A1  Aug. 2, 2018

Related U.S. Application Data

(60) Provisional application No. 62/197,612, filed on Jul. 28, 2015.

(51) Int. Cl.
*A61B 10/02* (2006.01)
*A61B 90/00* (2016.01)
*A61B 34/20* (2016.01)

(52) U.S. Cl.
CPC .......... *A61B 10/0233* (2013.01); *A61B 34/20* (2016.02); *A61B 90/37* (2016.02);
(Continued)

(58) Field of Classification Search
CPC ..... A61B 90/37; A61B 34/20; A61B 10/0233; A61B 2034/2065; A61B 2090/3782
See application file for complete search history.

(56) References Cited

U.S. PATENT DOCUMENTS 3,885,090 A * 5/1975 Rosenbaum ..... G08B 13/19669
360/5
8,460,182 B2 6/2013 Ouyang et al.
(Continued)

FOREIGN PATENT DOCUMENTS

EP   2777564 A1   9/2014

*Primary Examiner* — Bo Joseph Peng
(74) *Attorney, Agent, or Firm* — Sherry Austin

(57) ABSTRACT

An interventional instrument (16) is inserted into a patient (14) to perform an interventional medical procedure guided by a medical imaging device (10). A trigger control (26) is activated. An electronic data processing device (30) is programmed to operate the medical imaging device to: acquire and display video (50) of the interventional instrument (16) inserted into the patient; detect activation of the trigger control; in response to the detecting, process a video segment (54) of the acquired video to identify a trigger image (60) as a frame of the video segment capturing a medical intervention event performed by the interventional instrument and a location (62) of the medical intervention event in the identified trigger image; and display a still image of the identified trigger image with a superimposed marker (102) indicating the identified location of the medical intervention event.

18 Claims, 4 Drawing Sheets

(52) U.S. Cl.
    CPC ............... *A61B 2034/2065* (2016.02); *A61B 2090/3782* (2016.02)

(56) References Cited

U.S. PATENT DOCUMENTS

| | | | |
|---|---|---|---|
| 8,731,264 B2 | 5/2014 | Kruecker et al. | |
| 8,805,003 B2 | 8/2014 | Villain | |
| 9,814,442 B2 | 11/2017 | Kruecker | |
| 10,524,768 B2 | 1/2020 | Yoshida | |
| 2004/0057621 A1* | 3/2004 | Lee | G06V 10/7515 382/215 |
| 2005/0182316 A1 | 8/2005 | Burdette et al. | |
| 2007/0265525 A1* | 11/2007 | Sun | G06T 7/74 600/420 |
| 2011/0230768 A1 | 9/2011 | Nir | |
| 2013/0289393 A1* | 10/2013 | Kruecker | A61B 10/0275 600/424 |
| 2013/0338477 A1 | 12/2013 | Glossop et al. | |
| 2014/0135618 A1* | 5/2014 | Abe | A61B 6/463 600/424 |
| 2014/0275971 A1 | 9/2014 | Brown et al. | |
| 2015/0005621 A1 | 1/2015 | Liu | |
| 2015/0065803 A1* | 3/2015 | Douglas | G06K 9/6267 600/200 |
| 2015/0265368 A1* | 9/2015 | Chopra | A61B 1/045 600/424 |
| 2016/0030021 A1 | 2/2016 | Pasternak et al. | |

\* cited by examiner

WORKFLOW OF NEEDLE TIP IDENTIFICATION FOR BIOPSY DOCUMENTATION

CROSS-REFERENCE to PRIOR APPLICATIONS

This application is the U.S. National Phase application under 35 U.S.C. § 371 of International Application Ser. No. PCT/IB2016/054259, filed on Jul. 18, 2016, which claims the benefit of U.S. patent application Ser. No. 62/197,612, filed on Jul. 28, 2015. This application is hereby incorporated by reference herein.

FIELD

The following relates generally to the imaging-guided surgical arts such as biopsy arts, brachytherapy arts, and the like.

BACKGROUND

Imaging-guided surgical procedures are used for diverse purposes such as tissue sample extraction (i.e. biopsy) procedures, targeted laser ablation procedures, and brachytherapy procedures (in which radioactive seeds are delivered to targeted locations). An example of such a procedure is a prostate biopsy procedure. Prostate cancer affects one in six men in the United States, and in year 2014 was the second leading cause of cancer death in American men. Prostate biopsy is typically performed under ultrasound imaging guidance, using brightness-mode ("B"-mode) ultrasound video imaging to assist the urologist in targeting known lesions or other suspicious prostate regions for biopsy. A known system for ultrasound-guided prostate biopsy is the UroNav™ system (available from Invivo Corp., Gainsville, Fla., USA), which employs a reference image acquired by magnetic resonance imaging (MRI) and fused (i.e. spatially registered) with the ultrasound imaging. This allows precision-targeting of lesions identified on MRI, without the need for an MRI in-gantry procedure. In addition to the point targets identified through MRI, the UroNav™ system can also be used for guiding systematic sextant biopsies with the predefined prostate zones. In other known ultrasound-guided prostate biopsy systems, the reference frame is provided by an initially acquired three-dimensional ultrasound reference image, or the biopsy samples are referenced to a robotic manipulator reference frame.

Regardless of the choice of reference frame, meticulous documentation of biopsy locations is instrumental in longitudinal management of patients with likely or confirmed prostate cancer. With proper biopsy sample (i.e. core) location documentation, suspicious findings, or findings of low-grade cancer, can be followed up with repeat biopsies in the same locations in regular intervals (e.g. 6 or 12 months) to monitor for potential changes and deterioration of the condition; or, benign findings can be used to deliberately sample new, previously unsampled locations in order to maximize the likelihood of cancer detection on repeat biopsy. Such approaches can help steer away patients from unnecessary radical therapy and toward "active surveillance" or loco-regional therapy with reduced side-effects, cost, and impact on the quality of life A key step in accurately documenting a biopsy location is precise identification of an ultrasound video frame that clearly images the biopsy needle tip after firing, and accurate identification of the needle tip in this image. Correlation with the reference MRI image (in the UroNav™ system) or other reference then provides the biopsy location in the reference image space. However, the task of documenting biopsy locations can be tedious, and involves careful coordination between the urologist performing the biopsies and the assistant operating the ultrasound imaging system. As soon as a biopsy needle has been fired to obtain a tissue sample, the ultrasound video acquisition needs to be paused. The ultrasound frame showing the deployed needle is then selected visually, by cycling through the ultrasound video frames until a frame is identified in which the urologist clearly observes the biopsy needle. Thereafter, the needle tip is localized in the selected frame, for example using a mouse or trackball or touchscreen to mark the needle tip in a "frozen" display of the selected frame. Each of these steps slows down the biopsy workflow, requires training, and is operator-dependent and prone to operator error.

While prostate biopsy is described herein as an illustrative example, the skilled artisan will readily appreciate that similar difficulties arise in documenting locations of other image-guided surgical procedures employing medical imaging video guidance. For example, the disclosed techniques are readily applied to biopsy procedures of the prostate, liver, or other organs or tissues, as well as to other image-guided surgical procedures such as brachytherapy procedures.

The following discloses a new and improved systems and methods that address the above referenced issues, and others.

SUMMARY

In one disclosed aspect, a device is configured to operate in conjunction with an interventional instrument inserted into a patient to perform an interventional medical procedure. The device comprises a medical imaging device including a display component, a trigger control, and an electronic data processing device. The electronic data processing device is programmed to operate the medical imaging device to provide image guidance and location documentation for the interventional medical procedure by guidance and location documentation operations including: causing the medical imaging device to acquire and display video of the interventional instrument inserted into the patient; detecting activation of the trigger control; in response to the detecting, processing a video segment of the acquired video to identify a trigger image as a frame of the video segment capturing a medical intervention event performed by the interventional instrument and a location of the medical intervention event in the identified trigger image; and causing the medical imaging device to display a still image of the identified trigger image with a superimposed marker indicating the identified location of the medical intervention event.

In another disclosed aspect, a biopsy guidance and location documentation device comprises a trigger control and an ultrasound imaging device including a display component and an electronic processor. The ultrasound imaging device is configured to perform a method including: acquiring and displaying video of human anatomy being biopsied; detecting a biopsy trigger signal generated by user activation of the trigger control; processing the acquired video to automatically identify a trigger image as a frame of the video showing a fired biopsy needle tip and a location of the fired biopsy needle tip in the identified trigger image; and displaying the automatically identified trigger image as a still image with a superimposed marker indicating the automatically identified location of the fired biopsy needle tip.

In another disclosed aspect, a biopsy device comprises a biopsy needle assembly configured to fire the biopsy needle to collect a biopsy sample, and the biopsy guidance and location documentation device of the immediately preceding paragraph. In some such biopsy devices, the biopsy device further comprises a transrectal ultrasound probe configured for insertion into the rectum of a patient, with the biopsy needle assembly being secured with the transrectal ultrasound probe for insertion into the rectum of the patient and/or combined with a positioning device such as a transperineal grid plate with the rectal ultrasound probe.

In another disclosed aspect, a biopsy guidance and location documentation method comprises: acquiring and displaying, on a display device, medical imaging video of human anatomy being biopsied; detecting a trigger signal; in response to detecting the trigger signal, processing the acquired medical imaging video to identify a trigger image as a frame of the medical imaging video showing a fired biopsy needle tip and a location of the fired biopsy needle tip in the identified trigger image; and replacing the video displayed on the display device with a still image display of the identified trigger image with a superimposed marker indicating the identified location of the fired biopsy needle tip.

One advantage resides in providing a more efficient biopsy workflow.

Another advantage resides in providing more accurate identification of biopsy locations.

Another advantage resides in providing reduced likelihood of erroneous biopsy location identification.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
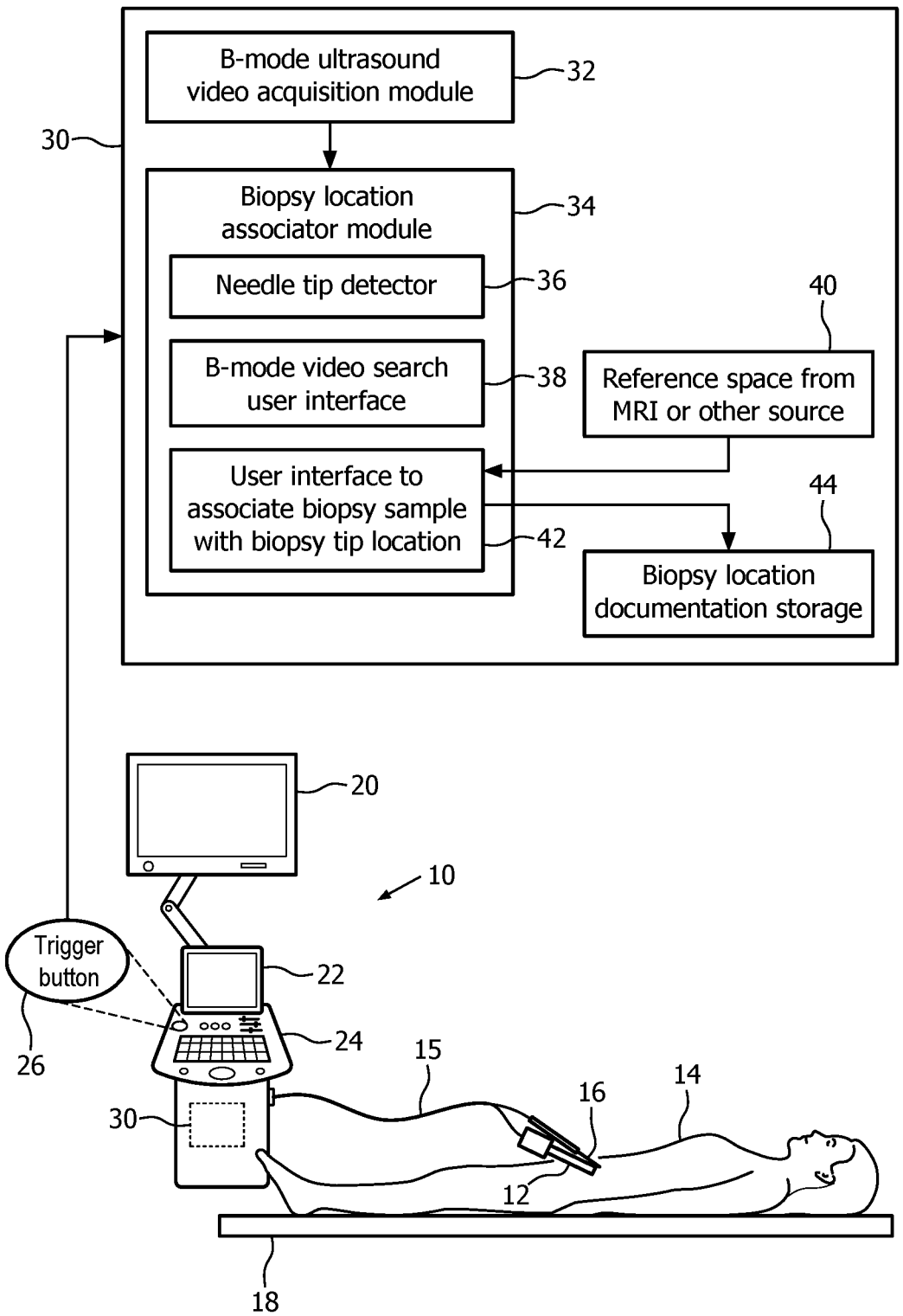
FIG. 1 diagrammatically illustrates an ultrasound-guided prostate biopsy system providing biopsy location documentation as disclosed herein.

With reference to FIG. 1, an illustrative ultrasound-guided prostate biopsy system is shown. An ultrasound imaging system 10 provides image guidance for targeting known lesions or other suspicious prostate regions for biopsy. The ultrasound imaging system 10 may, for example, be an EPIQ™ ultrasound imaging system available from Koninklijke Philips N. V., Eindhoven, the Netherlands, or may be another commercial or custom-built ultrasound imaging system. A rectal ultrasound probe 12 is inserted into the rectum of a patient 14. (The lower half of the patient is cut away in diagrammatic FIG. 1 to reveal the inserted probe 12 which would otherwise be occluded from view. Typically, the patient is lying on the side or facing up with the legs lifted up and fixed on a table extension.) The illustrative ultrasound probe 12 is connected with the ultrasound imaging system 10 via cabling 15. The illustrative ultrasound probe 12 includes an integrated biopsy needle assembly 16 for collecting biopsy samples. More generally, any type of image-guided biopsy technique may be employed, e.g. a transrectal ultrasound-guided biopsy using the integral probe 12, 16 as illustrated in which the ultrasound probe is inserted into the rectum and accesses the prostate via the rectal wall; or a transperineal biopsy in which the ultrasound probe is passed into the rectum but the biopsy needle passes through the perineum to access the prostate (optionally using a stereotactic grid plate or the like); or so forth. For the illustrative transrectal prostate biopsy procedure, the patient 14 lies on his side (as diagrammatically indicated in FIG. 1) on a diagrammatically indicated patient bed or support 18 with suitable pillows or other supports (not shown). The illustrative ultrasound imaging system 10 includes a display component 20 for displaying ultrasound images, and one or more user interfacing components such as a user interface display 22 and user control panel 24 including user input devices such as a keyboard, dedicated buttons, a trackball or mouse or other pointing device, or so forth. Instead of or in addition to a pointing device, one or both display components 20, 22 may be a touchscreen display enabling user input by pressing a location on the display 20.

In order to target a lesion or other tissue, the urologist (or, more generally, a medical professional) manipulates the probe assembly 12, 16 to align it with the target while the ultrasound imaging system 10 operates in a video mode, for example providing brightness mode (B-mode) imaging frames at a high frame rate of, for example, on the order of 15-30 frames per second. The urologist views the ultrasound display 20 showing the B-mode video while manipulating the probe assembly 12, 16 in order to receive (near) real-time feedback enabling precise targeting of the lesion or other target tissue. When the urologist is satisfied that the target is in proper alignment, the urologist fires the biopsy needle to acquire the biopsy sample. The urologist then immediately withdraws the biopsy needle with the captured biopsy core and stores the core in a biopsy specimen container. As described next, the system of FIG. 1 provides automated or semi-automated documentation of the biopsy location, so that the urologist can concentrate on performing the biopsy sample recovery and storage actions and then can review the proposed biopsy location association, correct it if necessary, and associate the finally chosen location with the biopsy sample.

The user control panel 24 includes a trigger control 26 for triggering the biopsy location association. The illustrative trigger control 26 is a "biopsy" button 26 diagrammatically shown in enlarged isolation in FIG. 1 for illustrative purposes. It will be appreciated that the trigger control 26 could take other forms, such as a handheld remote control in wireless radio or infrared contact with the ultrasound imaging system 10, a soft key shown in the user interface display 22 (which in this case would be touch-sensitive), or so forth. When the biopsy button 26 is pressed, a biopsy location association operation is performed. To this end, the ultrasound imaging system 10 further includes a microprocessor, microcontroller, or other electronic data processing component 30 which is diagrammatically indicated in FIG. 1.

While the illustrative electronic processor 30 comprises a microprocessor or microcontroller housed inside the ultrasound imaging system 10, in other embodiments the electronic processor may have another physical architecture, such as being a desktop or notebook computer connected by a video cable with the ultrasound imaging system to receive, process, and display video acquired by the ultrasound imaging system. The illustrative electronic processor 30 is programmed to implement a B-mode ultrasound video acquisition module 32 that causes the ultrasound imaging system 10 to acquire B-mode video and display the acquired B-mode video on the display component 20 for viewing by the urologist or other medical professional. When the urologist presses the trigger button 26, the electronic processor 30 detects this trigger signal. Upon receipt of the trigger signal, the ultrasound imaging system 10 continues to acquire video content for some predetermined time interval (or, alternatively measured, for some predetermined number of frames at a given frame rate) where the predetermined time interval is sufficiently long to capture the firing of the biopsy needle tip into the tissue being biopsied. Thereafter, a biopsy location associator module 34 processes this video segment acquired after activation of the biopsy button 26 in order to determine a biopsy location. The illustrative biopsy location associator module 34 includes an automatic needle tip detector 36 that processes the frames of the video segment in order to identify a "trigger" frame (or trigger image) that best captures the fired biopsy needle tip, and to identify the biopsy needle tip location in that trigger image. This automatic identification can be done, for example, by matching a linear biopsy needle tip pattern oriented at the appropriate firing angle (known due to the orientation of the rectal ultrasound probe/biopsy needle assembly 12, 16) to a most prominent linear feature in each image frame.

The automatically identified trigger frame is displayed on the display component 20 of the ultrasound imaging system 10 as a still image display (also sometimes referred to as a still frame display)—that is, the trigger frame is displayed as a static image. Additionally, a marker indicating the automatically identified needle tip location is superimposed on the still image display of the trigger image. It will be appreciated that since the needle tip detection process is fast, from the viewpoint of the urologist the B-mode video on the display 20 is replaced by the still image display of the trigger image only a few moments, or even apparently instantaneously, after activating the trigger control 26. The urologist then reviews the displayed trigger image with the superimposed marker. In one embodiment the superimposed marker is a dotted or dashed line, or is displayed as a translucent or semi-transparent marker, so that the underlying needle tip image can be seen behind it; additionally or alternatively, the urologist can toggle between showing or hiding the superimposed marker using a suitable toggle control or button of the user input panel 24. If the urologist is satisfied with the displayed result, the urologist can accept it by suitable input via a user input device (e.g. clicking on an "accept" button shown on the display using a mouse or trackball). On the other hand, if the urologist is unsatisfied with the automatically identified trigger image and/or the identified biopsy needle tip location, the urologist may invoke a video search user interface 38 in order to flip through the frames of the video segment acquired after triggering the biopsy needle firing in order to manually find a different trigger image that is preferred by the urologist. This manual search preferably starts with the automatically identified trigger image, which is likely to be at least close in the sequence of frames making up the video segment to the "best" image as judged by the urologist.

In this way, user input is received via a user input component 22, 24 of the ultrasound imaging device 10 that identifies a documented location of the fired biopsy needle tip as one of (i) the location of the fired biopsy needle tip automatically identified via the needle tip detector 36 or (ii) a manually identified location of the fired biopsy needle tip in a manually identified trigger image identified from the video by the urologist using the search user interface 38. Thereafter, the documented location of the fired biopsy needle tip in the reference frame of the medical imaging device 10 is transformed to a documentation reference frame or space 40. This reference space 40 may be variously defined. For example, the reference space 40 may be defined in terms of a reference magnetic resonance image that is fused with the ultrasound images. This choice of reference frame is provided by the UroNav™ system. Advantageously, suspicious lesions may be readily identified in the magnetic resonance image so that the UroNav™ system can superimpose these on the B-mode video during the lesion targeting phase. In another approach, the reference frame 40 is defined in terms of a three-dimensional reference ultrasound image acquired using the ultrasound imaging system 10 before commencing the biopsy procedure. As yet another example, the reference frame 40 may be defined in terms of a mechanical framework of a robotic manipulator used to position the rectal ultrasound probe/biopsy needle assembly 12, 16.

With the documented biopsy location determined in the documentation reference frame, the urologist then uses a user interface 42 to associate the biopsy sample with the documented location, and the documented biopsy location in the documentation reference frame 40 is recorded in a biopsy location documentation storage 44. The documentation storage 44 may, for example, be a local storage medium such as a hard disk of the ultrasound imaging system 10, and/or may be network data storage such as an Electronic Medical Record (EMR) or Electronic Health Record (EHR). In making the biopsy sample/documented biopsy location association, the urologist may suitably use a biopsy sample indexing number from the biopsy specimen container or any other auditable biopsy sample identification framework.

In some embodiments, the trigger control 26 solely operates to trigger execution of the fired biopsy needle tip location association processing performed by the electronic processor 30. In such embodiments, the urologist first operates a separate control (not shown) to fire the biopsy needle tip to acquire a biopsy sample. Immediately thereafter, the urologist (or an assistant) activates the trigger control 26 to execute the biopsy needle tip location association function of the ultrasound imaging system 10.

In other embodiments, including the illustrative embodiment, the trigger control 26 also triggers the biopsy needle tip assembly 16 to fire the biopsy needle tip to acquire the biopsy sample. In these embodiments, a trigger signal generated by activation of the illustrative trigger control 26 is conveyed via the cabling 15 to the ultrasound probe assembly 12, or more particularly to the biopsy needle assembly 16, and triggers the biopsy needle tip assembly 16 to fire a biopsy needle tip into the lesion to acquire a biopsy core (i.e. biopsy sample). Concurrently, the activation of the trigger control 26 also initiates the biopsy tip location association operation. This operation includes, as an initial step, continuing the video collection for a time interval (or, equivalently, number of frames) that is long enough to capture images of the fired biopsy needle tip. This time interval is short, e.g. a fraction of a second to a few seconds, as it merely needs to span the time for the biopsy needle to fire and embed into the target tissue. After activating the trigger control 26 to fire the biopsy needle tip and initiate the tip location association operation, the urologist retrieves the fired needle tip containing or holding the biopsy sample via a biopsy needle guide and places the biopsy sample into a biopsy specimen container.

Figure 2:
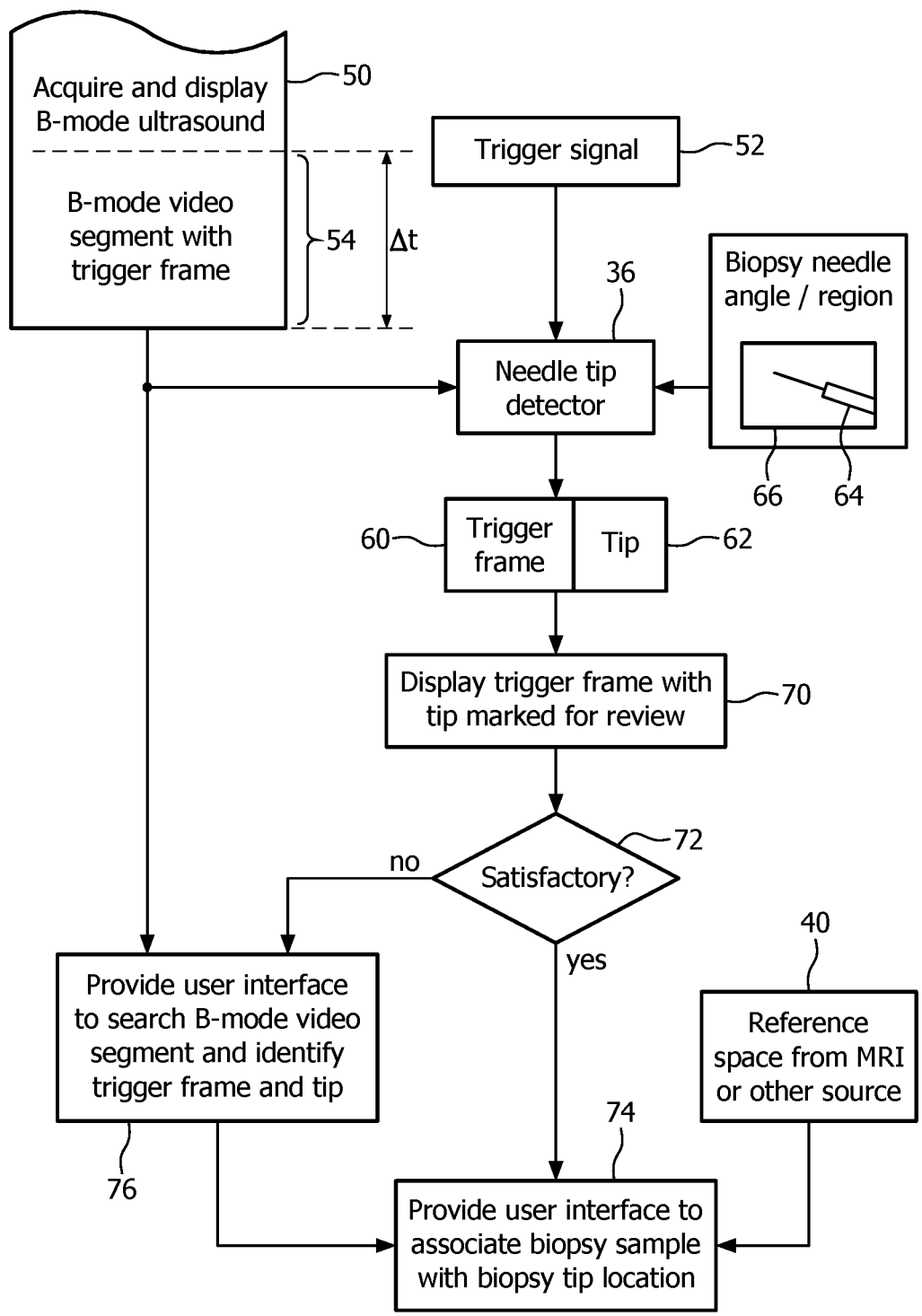
FIG. 2 diagrammatically illustrates a biopsy sample acquisition method including biopsy location documentation suitably performed using the system of FIG. 1.

With continuing reference to FIG. 1 and with further reference to FIG. 2, a biopsy guidance and location documentation workflow performed using the system of FIG. 1 including the ultrasound system 10 and the processor 30 is described. B-mode video 50 is continuously acquired and displayed to provide image guidance for targeting the biopsy needle. After the urologist has aligned the target tissue, the biopsy needle tip is fired, for example using a handheld biopsy gun having a firing button (features not shown). After firing the biopsy needle, the trigger button 26 of the ultrasound device 10 is pressed to generate a trigger signal 52 that starts the biopsy needle tip location and documentation procedure. After trigger signal 52 is output, the video acquisition continues for a time interval Δt (which may be measured in time units or as a number of B-mode video frames based on a frames/second rate). Thus, a video segment 54 is acquired after the trigger signal 52 is detected, which images the previously triggered biopsy needle tip that is now embedded in the target tissue.

In some alternative embodiments, the firing of the biopsy needle tip also triggers the start of the biopsy needle tip location and documentation procedure. In other words, in these embodiments the same trigger control is actuated to simultaneously trigger both the biopsy needle firing and the start of the documentation procedure. In such embodiments, the time interval Δt starts at the same time as the initiation of the biopsy needle firing, and so Δt in these embodiments should be long enough to encompass the firing time and capture the needle tip after it has come to rest embedded into the target tissue.

Regardless of whether the biopsy needle tip is fired by the trigger control 26 or by a separate control, the video segment 54 which images the fired biopsy needle tip is analyzed on a frame-by-frame basis by the needle tip detector 36 to automatically identify a trigger frame 60 showing the fired needle tip, and the needle tip location (i.e. tip) 62 is identified in the trigger frame or image 60. The needle tip detector 36 suitably leverages a needle tip pattern 64 having a known angle, and optionally further leverages a priori knowledge that the needle tip is in a known general region 66. Such localization to a known region 66 sets the search area within a video frame segment to optimize the performance of the needle tip detector 66. For example, in embodiments providing guidance and documentation for a transperineal biopsy procedure employing a grid plate, the grid location of the biopsy defines the a priori known region 66. This information 64, 66 is provided based on the approximately known position and orientation of the rectal probe assembly 12, 16. For example, the needle tip pattern 64 can be scanned over each video frame with a suitable comparison metric (e.g., a sum of |image pixel-pattern pixel|) used to assess whether a match is found.

With continuing reference to FIGS. 1 and 2, in an operation 70 the trigger frame 60 is displayed with a superimposed marker indicating the identified tip 62. The urologist then makes a decision 72 as to whether to accept this automatically identified biopsy needle tip location 62. If it is accepted, then in an operation 74 the association user interface 42 is invoked to perform the biopsy sample/biopsy location association, including transforming from the ultrasound image frame space to the reference space 40, as already described. On the other hand, if the decision 72 is that the automatically identified needle tip location 62 is not satisfactory, then in an operation 76 the video search user interface 38 is invoked via which the urologist manually searches the video segment 54 frame-by-frame to manually choose the documentation trigger frame and then manually identifies the biopsy needle tip location in this frame. The manually identified tip location is then associated to the biopsy sample via operation 74 as already described.

Figure 3:
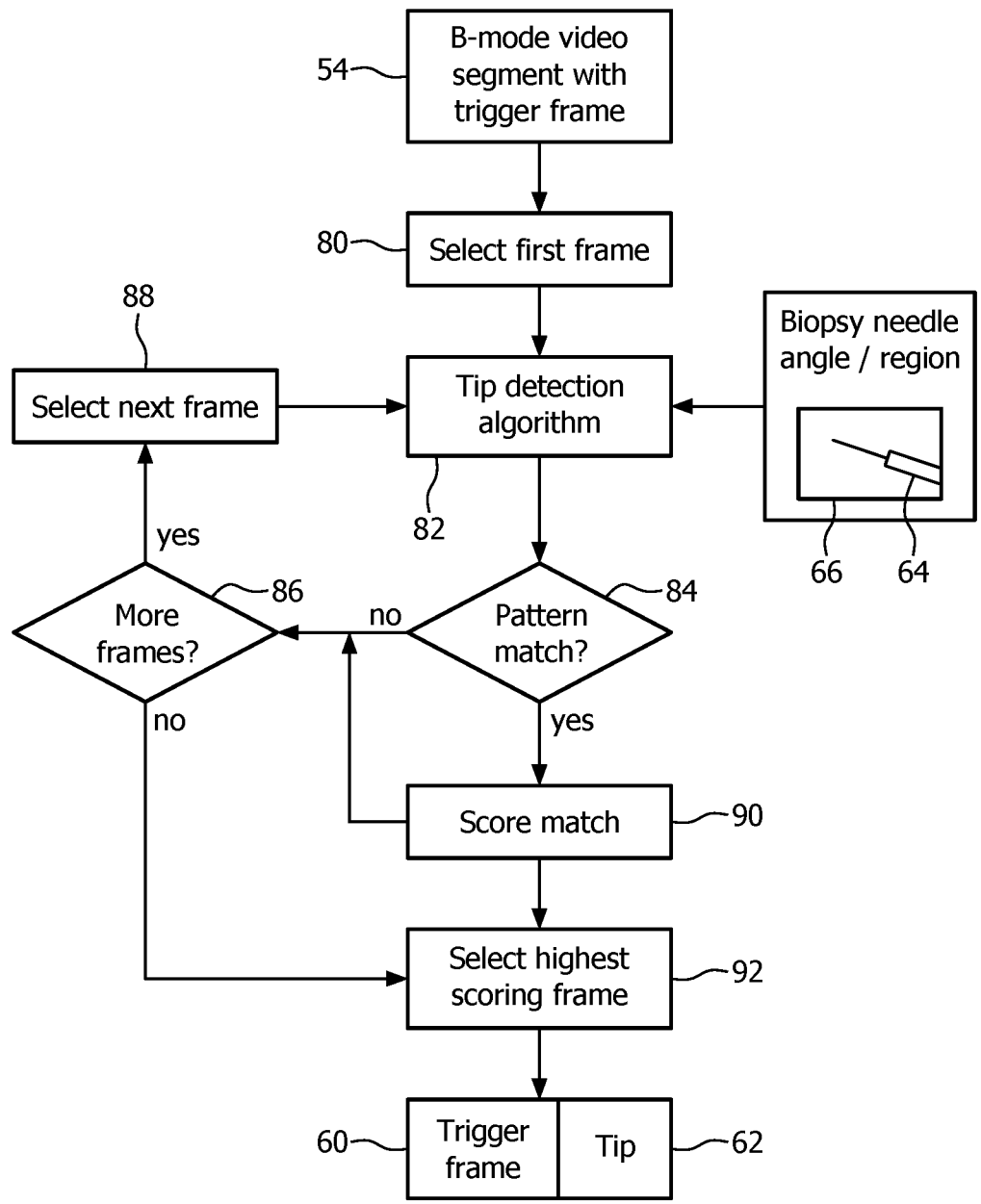
FIG. 3 diagrammatically illustrates a flow chart of a suitable implementation of the needle tip detection employed in FIGS. 1 and 2.

With reference to FIG. 3, an illustrative needle tip detection approach suitably performed by the needle tip detector 36 is described. In an operation 80, a first frame is selected from the video segment 54. A tip detection algorithm 82 is then applied, which in the illustrative example attempts to match the biopsy needle tip pattern 64 at its known angle to a linear feature in the video frame under analysis. In a decision 84 it is determined whether this attempt at finding the needle tip in the image frame was successful. If not, then flow passes to decision 86 where it is determined if there are more frames to analyze in the video segment 54, and if so a next frame is selected in operation 88.

If the decision 84 determines that the attempt to identify the tip in the frame currently under analysis was successful, then flow passes to a scoring operation 90 which scores the match using some quantitative metric as to likelihood that the biopsy needle tip location has been accurately identified. For example, the metric may sum the difference, on a pixel-by-pixel basis, between the pixel value of the pattern 64 and the value of the corresponding pixel in the matched linear feature of the frame under analysis. In another approach, the metric may measure aspects of the matched linear feature of the frame under analysis such as its width and length, and compare these with the pattern width and length. After all frames of the video segment 54 have been analyzed, in an operation 92 the highest-scoring frame is identified as the trigger frame or image 60, and the biopsy needle tip location 62 is identified in this trigger frame 60.

Figure 4:
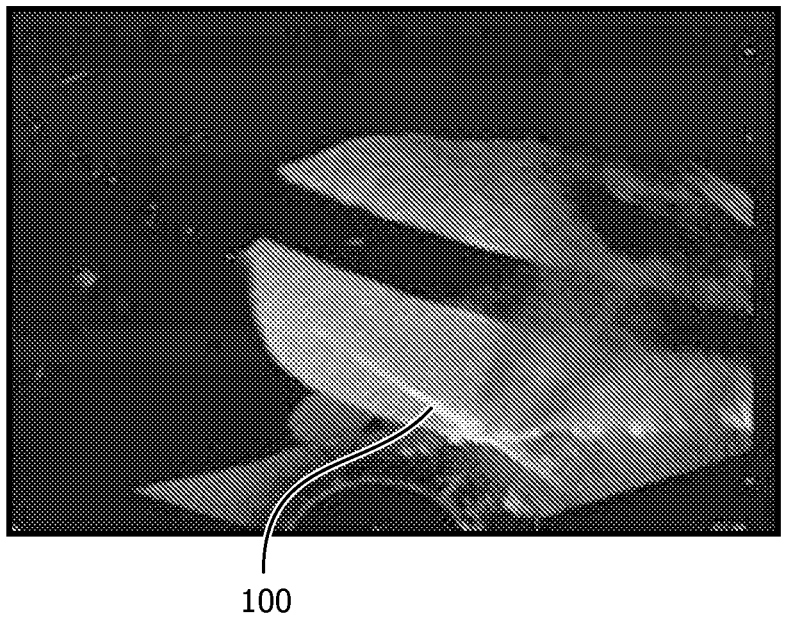
FIG. 4 illustrates a trigger frame identified in a phantom using the implementation of FIG. 3.
Figure 5:
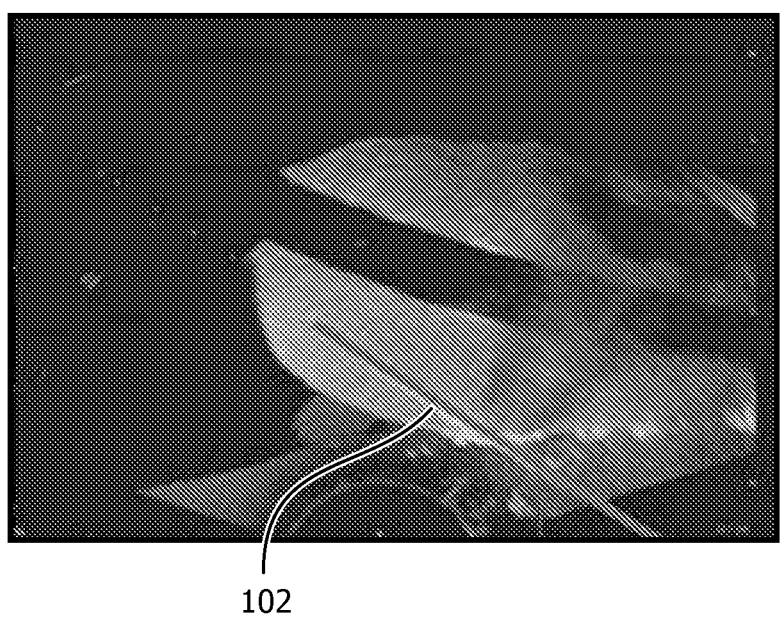
FIG. 5 illustrates the trigger frame of FIG. 4 with a superimposed linear marker indicating the needle.

With reference to FIGS. 4 and 5, an example of a biopsy needle tip identification is shown, for an imaged phantom. FIG. 4 shows the image including a linear feature 100 that is likely to be the biopsy needle tip. FIG. 5 shows the same image with a marker 102 superimposed indicating the identified biopsy needle tip location.

In the following, some further illustrative embodiments are described.

In one approach, a user input-triggered needle tip detection is provided. A user (e.g. urologist) determines when to start the automatic needle tip detection. In the illustrative embodiments, this determination is advantageously automatically made by pressing the biopsy button 26 which also triggers the firing of the biopsy needle tip. In other embodiments, separate controls are employed, the first control being activated to fire the biopsy needle tip into the tissue and the second control triggering start of the tip location association procedure. In either case, an image processing-based automatic needle tip detection algorithm is applied to detect needle tips from a set of given image frames (e.g. the video segment 54) and return the frame number of the needle firing frame (i.e. the trigger frame 60). If the urologist is unhappy with the automatically selected trigger frame and tip location, then a user interface (UI) 38 enables the operator (e.g. urologist) to manually select the needle firing frame and adjust the needle tip position. A UI 42 enables the operator to associate the biopsy core to the automatically or manually identified tip location.

The needle tip detector 36 receives a group of N ultrasound frames making up the video segment 54, at least some of which show the fired biopsy needle tip embedded in the tissue from which the biopsy sample is being acquired. Other input data like the biopsy guide line (expected path of the biopsy needle, e.g. the angle or direction of the needle tip pattern 64) and parameter settings are also optionally provided to the needle tip detector 36. The output of the needle tip detector 36 includes a needle tip location $L_i$, $0<i<N+1$ with corresponding needle score $S_i$, $0<i<N+1$ for each frame in the segment (or at least for each frame in which the tip detection algorithm 82 successfully located the needle tip; in some embodiments any frames in which the tip detection algorithm 82 failed to locate the needle tip are assigned a score of zero). A detected firing frame $N_{firing}$ is identified for the video segment 54, which is the frame having the highest score value (highest $S_i$). The score is a metric of how likely it is that the detected signal actually stems from the needle tip. In one suitable approach, the tip detection algorithm 82 first tries to detect the needle in each single frame in a pre-defined region 66, and the needle score is computed based on the level of confidence in the detection in any given frame. The ultrasound frame most likely showing the actual needle firing is then determined at the end. Once the needle tip is detected, the live imaging stream is frozen as the firing ultrasound frame of $N_{firing}$ identified by the needle tip detector 36 is displayed as a still frame. (Alternatively, the system may initially display the last frame, i.e. the frame when the urologist manually triggered the algorithm). A visualized needle tip marker, which can be a highlighted graphical object like a yellow bar (optionally translucent or partially transparent, and/or showed as a dashed or dotted line, so as to reveal the underlying image feature that was detected as the needle tip), is displayed at the detected needle tip location $L_{firing}$. The urologist may then examine the identified firing ultrasound frame and also the marked identified needle tip location. If the result is satisfactory, the urologist accepts the automatically identified tip location $L_{firing}$ and processing moves to the association operation 74. Otherwise, the urologist can choose to adjust it (i.e. manually identify the tip location) via the search user interfacing operation 76.

In a suitable embodiment of this tip search user interfacing operation 76, the first operation to perform is to manually identify the needle firing frame. The search user interface 38 enables the urologist to move from one frame to another. For example, in one specific user device implementation, the urologist can either use a middle wheel of a (not shown) mouse to scroll through the frames, or move a scroll bar displayed at the right side edge of a viewing panel displayed on the display 20. As the urologist goes through difference frames, the detected needle tip location for each frame is displayed (e.g. output by the pattern matching operations 82, 84 of FIG. 3 for each analyzed frame). When the urologist stops at a frame, if the urologist is satisfied with the needle tip position in that frame then the adjustment is finished and the workflow proceeds to the association operation 74. Otherwise, the user can further choose to adjust the needle tip in the manually identified trigger image.

If the urologist chooses to adjust the marker position in the provided user interface 38 is again used, for example in a specific embodiment the urologist uses the mouse to click at a desired location in the view panel, which will bring the marker to the position. The urologist may also first point the mouse at the biopsy guideline and then scroll the middle wheel, which will move the marker back and forth along the biopsy guide line until it is at the desired position.

In the association operation 74, the urologist associates the documentation biopsy needle tip location (i.e. the automatically or manually identified biopsy needle tip location) to the aimed target/zone. In one suitable approach, a list of targets or zones identified from the reference MRI image or other reference space 40 is displayed. The association user interface 42 enables the urologist to browse and select the appropriate target for biopsy. When a biopsy sample acquisition is performed and the needle tip has been labeled, the urologist suitably associates the biopsy with the target or zone. In some embodiments, the urologist also has the option to add a new target label for the biopsy into the record. If the targets are predefined in a desired order, the system can be configured to advance to the next target automatically for the user. The association data are stored in the documentation storage 44.

An alternative embodiment (not shown) does not include the automatic needle tip detector 36. In this case, a variant biopsy needle tip location association procedure can be employed. In this variant procedure, the needle tip location $L_i$ is set to a fixed position, for example the mean position of the needle tips from a training data set. The needle score $S_i$ is set to a constant number and then $N_{firing}$ is the last frame in the group.

While the illustrative interventional procedure is a transrectal prostate biopsy procedure, it will be appreciated that the disclosed image guidance and location documentation devices and methods may be readily employed in biopsy procedures for other human anatomy, such as other organs like the liver, and/or using other access pathways such as trans-perineal Bx access.

It will be further appreciated that the disclosed image guidance and location documentation devices and methods may be readily employed in other types of interventional procedures, such as in brachytherapy procedures in which the interventional instrument is a brachytherapy seed delivery instrument and the medical intervention event corresponding to the firing of a biopsy needle tip is the depositing of a radioactive seed by the brachytherapy seed delivery instrument.

It will be further appreciated that the disclosed image guidance and location documentation devices and methods may be readily employed in conjunction with image-guided interventional medical procedures using guidance medical imaging modalities other than ultrasound. For example, the medical imaging modality may be computed tomography (CT) or cone-beam CT or magnetic resonance imaging (MRI).

It will be yet further appreciated that the disclosed processing operations performed by the electronic processor 30 may be embodied by a non-transitory storage medium storing instructions that are readable and executable by the microprocessor, microcontroller, or other electronic data processing component 30 to perform these operations. Such non-transitory storage medium may, by way of non-limiting illustration, include a hard disk drive or other magnetic storage medium, a flash memory, read-only memory (ROM) or other electronic storage medium, an optical disk or other optical storage medium, various combinations thereof, or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A device operable in conjunction with an interventional instrument inserted into a patient to perform an interventional medical procedure, the device comprising:
   an ultrasound imaging device including a display component;
   a trigger control that is activatable by a user to control triggering of guidance and location documentation operations for the interventional medical procedure, the trigger control comprising a button or a touch-sensitive key; and
   a processor to operate the ultrasound imaging device to provide image guidance and location documentation for the interventional medical procedure by the guidance and location documentation operations including:
   causing the ultrasound imaging device to acquire and display video of the interventional instrument inserted into the patient;
   detecting activation of the trigger control;
   in response to the detecting, processing a video segment of the acquired video to identify a trigger image as a frame of the video segment, the trigger image capturing a medical intervention event performed by the interventional instrument and a location of the medical intervention event, the processing comprising matching a linear interventional instrument pattern to a linear feature in each of plural frames of the video segment that each show the medical intervention event performed by the interventional instrument and the location and selecting one of the plural frames as the trigger image, the trigger image selected based on a pattern matching score; and
   causing the ultrasound imaging device to display a still image of the trigger image with a superimposed marker indicating the identified location of the medical intervention event.

2. The device of claim 1, wherein
   the interventional instrument comprises a biopsy instrument and the medical intervention event comprises firing of a biopsy needle by the biopsy instrument to acquire a biopsy sample.

3. The device of claim 1, wherein the guidance and location documentation operations further include:
   receiving, via one or more user input devices of the ultrasound imaging device, an indication that the identified location of the medical intervention event is acceptable whereby the identified location of the medical intervention event is designated as the documented location of the medical intervention event in a reference frame of a medical imaging device.

4. The device of claim 3, wherein the guidance and location documentation operations further include:
   transforming the documented location of the medical intervention event in the reference frame of the medical imaging device to a documentation reference frame; and
   recording the documented location of the medical intervention event in the documentation reference frame.

5. The device of claim 1, wherein the still image display of the trigger image with the superimposed marker replaces the display of the video on the display component of the medical imaging device.

6. The device of claim 1, wherein the guidance and location documentation operations further include:
   selecting the video segment as a video segment consisting of a time interval or number of frames (Δt) starting at the detection of activation of the trigger control.

7. The device of claim 1, wherein the guidance and location documentation operations further include:
   receiving, via one or more user input devices of the ultrasound imaging device, an indication that the identified location of the medical intervention event is not acceptable, wherein the guidance and location documentation operations further include providing a user interface including a video segment browser, the user interface including a manual select, thereby enabling selection of the documented location of the medical intervention event in the reference frame of the medical imaging device.

8. The device of claim 7, wherein the guidance and location documentation operations further include:
   transforming the documented location of the medical intervention event in the reference frame of the medical imaging device to a documentation reference frame; and
   recording the documented location of the medical intervention event in the documentation reference frame.

9. The device of claim 1, wherein the processor includes an electronic data processing device.

10. The device of claim 1, wherein the interventional instrument comprises a therapy delivery instrument and the medical intervention event comprises delivering therapy by a therapy delivery instrument.

11. A biopsy guidance and location documentation device comprising:
    a trigger control comprising a button or a touch-sensitive key; and
    an ultrasound imaging device including a display component and an electronic processor, the ultrasound imaging device configured to:
    acquire and display video of human anatomy during a biopsy operation;
    detect a biopsy trigger signal generated in response to a user pressing the trigger control;
    process a video segment acquired in response to detection of the biopsy trigger signal to identify a trigger image as a frame of the video segment selected amongst plural frames of the video segment, the trigger image showing a fired biopsy needle tip and a location of the fired biopsy needle tip in the trigger image; and
    display the trigger image as a still image with a superimposed marker indicating the location of the fired biopsy needle tip.

12. The biopsy guidance and location documentation device of claim 11, wherein the ultrasound imaging device is further configured to:
    receive user input via a user input component of the ultrasound imaging device that identifies a documented location of the fired biopsy needle tip as one of (i) the automatically identified location of the fired biopsy needle tip and (ii) a manually identified location of the fired biopsy needle tip in a manually identified trigger image comprising a frame of the video;
    transform the documented location of the fired biopsy needle tip to a documentation reference frame; and
    record the documented location of the medical intervention event in the documentation reference frame in a biopsy location documentation storage.

13. The biopsy guidance and location documentation device of claim 12, wherein the documentation reference frame comprises a reference three-dimensional magnetic resonance image fused with the trigger image.

14. The biopsy guidance and location documentation device of claim 11, wherein the ultrasound imaging device is configured to process the acquired video to automatically identify the trigger image by:
attempting to identify the fired biopsy needle tip in each frame of the video segment;
scoring at least each frame in which the fired biopsy needle tip is successfully identified using a reliability metric for the fired biopsy needle tip identification; and
identifying the trigger image as the highest-scoring frame.

15. The biopsy guidance and location documentation device of claim 14, wherein attempting to identify the fired biopsy needle tip in each frame of the video segment comprises attempting to match a linear needle tip image pattern at a known biopsy needle tip angle or direction in each frame of the video segment.

16. The biopsy guidance and location documentation device of claim 11, wherein the ultrasound imaging device is further configured to:
terminate the acquiring and displaying of video at a time interval or number of frames ($\Delta t$) after detecting activation of the biopsy trigger control; and
select a video segment of the video for processing including the video frames acquired during the time interval or number of frames ($\Delta t$).

17. The biopsy guidance and location documentation device of claim 11, wherein the display of the trigger image replaces the display of the video.

18. The biopsy guidance and location documentation device of claim 11, wherein the trigger control triggers the firing of the biopsy needle tip, upon being pressed, to collect a biopsy sample.

* * * * *